(12) United States Patent
Gardner et al.

(10) Patent No.: US 12,193,821 B2
(45) Date of Patent: Jan. 14, 2025

(54) NEURAL INTERFACE DEVICE MANUFACTURING METHOD

(71) Applicants: Board of Regents, The University of Texas System, Austin, TX (US); Trustees of Boston University, Boston, MA (US)

(72) Inventors: Timothy James Gardner, Brookline, MA (US); Stuart F. Cogan, Dallas, TX (US)

(73) Assignees: Board of Regents, The University of Texas System, Austin, TX (US); Trustees of Boston University, Boston, MA (US)

( * ) Notice: Subject to any disclaimer, the term of this patent is extended or adjusted under 35 U.S.C. 154(b) by 430 days.

(21) Appl. No.: 17/559,835

(22) Filed: Dec. 22, 2021

(65) Prior Publication Data

US 2022/0110565 A1 Apr. 14, 2022

Related U.S. Application Data

(62) Division of application No. 16/015,878, filed on Jun. 22, 2018, now Pat. No. 11,224,371.

(Continued)

(51) Int. Cl.
*A61B 5/24* (2021.01)
*A61L 31/02* (2006.01)
(Continued)

(52) U.S. Cl.
CPC .............. *A61B 5/24* (2021.01); *A61L 31/022* (2013.01); *A61L 31/028* (2013.01); *A61L 31/06* (2013.01);
(Continued)

(58) Field of Classification Search
CPC . A61B 5/24; A61L 31/02; A61L 31/06; A61L 31/08; A61L 31/10; A61L 31/14; C23C 16/32

See application file for complete search history.

(56) References Cited

U.S. PATENT DOCUMENTS 5,755,759 A 5/1998 Cogan
8,738,110 B2 5/2014 Tabada et al.
(Continued)

FOREIGN PATENT DOCUMENTS

WO 2013010161 A2 1/2013
WO 2015003185 A2 1/2015

OTHER PUBLICATIONS

Diaz-Botia, et al.; "A silicon carbide array for electrocorticography and peripheral nerve recording"; Open Access; IOP Publishing; Journal of Neural Engineering; 14 056006; https://doi.org/10.1088/1741-2552/aa7698; 2017; 11 pgs.

(Continued)

*Primary Examiner* — Minh N Trinh

(57) ABSTRACT

Manufacturing a neural interface device. Forming a neural interface probe of an implantable microelectrode body. PECVD a first amorphous silicon carbide insulation layer, forming a thin film metal trace and interface pad on the first layer, the pad on a portion of the trace. PECVD a second amorphous silicon carbide insulation layer on the first layer and covering the trace and the pad. Forming an opening in the second layer to expose the pad to an ambient environment. Patterning the first and second layers to define the neural interface probe. The probe has a rectangular cuboid shape, a cross-sectional area perpendicularly transverse to a long axis length of the probe and through any perpendicularly transverse cross-section along the long axis length is (Continued)

less than about 50 microns. The layers are the principle material of construction of the probe.

5 Claims, 21 Drawing Sheets

Related U.S. Application Data

(60) Provisional application No. 62/523,825, filed on Jun. 23, 2017.

(51) Int. Cl.

| | | |
|---|---|---|
| *A61L 31/06* | (2006.01) | |
| *A61L 31/08* | (2006.01) | |
| *A61L 31/10* | (2006.01) | |
| *A61L 31/14* | (2006.01) | |
| *C23C 16/32* | (2006.01) | |
| *C23C 16/50* | (2006.01) | |
| *C23C 16/56* | (2006.01) | |
| *C23C 28/00* | (2006.01) | |
| *A61B 5/00* | (2006.01) | |
| *A61B 5/291* | (2021.01) | |

(52) U.S. Cl.
CPC .......... *A61L 31/088* (2013.01); *A61L 31/10* (2013.01); *A61L 31/14* (2013.01); *C23C 16/325* (2013.01); *C23C 16/50* (2013.01); *C23C 16/56* (2013.01); *C23C 28/00* (2013.01); *C23C 28/32* (2013.01); *C23C 28/341* (2013.01); *A61B 5/291* (2021.01); *A61B 5/6868* (2013.01); *A61B 2562/0209* (2013.01); *A61B 2562/043* (2013.01); *A61B 2562/125* (2013.01)

(56) References Cited

U.S. PATENT DOCUMENTS

| | | |
|---|---|---|
| 9,211,401 B2 | 12/2015 | Frewin et al. |
| 9,498,617 B2 | 11/2016 | Tabada et al. |
| 9,844,660 B2 | 12/2017 | Vetter et al. |
| 10,136,825 B2 | 11/2018 | Frewin et al. |
| 11,224,371 B2 * | 1/2022 | Gardner ................ A61L 31/022 |
| 2007/0219551 A1 | 9/2007 | Honour et al. |
| 2010/0198297 A1 | 8/2010 | Cogan et al. |
| 2011/0288391 A1 | 11/2011 | Rao et al. |
| 2013/0345780 A1 | 12/2013 | Tabada et al. |
| 2016/0220135 A1 | 8/2016 | Negi et al. |
| 2022/0110565 A1 * | 4/2022 | Gardner ................ C23C 16/56 |

OTHER PUBLICATIONS

Knaack, et al.; "In vivo Characterization of Amorphous Silicon Carbide As a Biomaterial for Chronic Neural Interfaces"; Frontiers in Neuroscience; vol. 10 | Article 301; doi: 10.3389/fnins.2016. 00301; Jun. 28, 2016; 12 pgs.

Lei, et al.; "SiC protective coating for photovoltaic retinal prosthesis"; IOP Publishing; Journal of Neural Engineering; 13 046016; doi:10.1088/1741-2560/13/4/046016; 2016; 12 pgs.

Frewin, et al.; "Sensory Motor Integration—Electrochemical Evaluation of Shape Memory Polymer Electrodes"; A Joint Meeting of NANA & NIC; Jun. 25-29, 2016; 1 pg.

Frewin, et al.; "Models and Stimulation Paradigms—Electrical Performance of Single Material Silicon Carbide (SiC) Microelectrodes" A Joint Meeting of NANS & NIC; Jun. 25-29, 2016; 1 pg.

Hsu, et al.; "Characterization of a Sicx:H thin films as an encapsulation material for integrated silicon based neural interface devices"; NIH Public Access—Author Manuscript—Thin Solid Films; Nov. 1, 2007; pp. 1-24.

Azevedo, et al.; "Silicon Carbide Coated MEMS Strain Sensor for Harsh Environment Applications"; Proceedings of the IEEE International Conference on Micro Electro Mechanical Systems (MEMS); dio:10.1109/MEMSYS.2007.4433166; Feb. 2007; 4 pgs.

Kalnins, et al.; "Clinical outcomes of silicon carbide coated stents in patients with coronary artery disease"; http://www.MedSciMonit. com/pub/vol_8/no_2/1900.pdf; Product Investigation; PMID: 11859292; 2002; pp. PI16-PI20.

Cogan, et al.; "Plasma-enhanced chemical vapor deposited silicon carbide as an implantable dielectric coating"; Wiley Periodicals, Inc.; 2003; pp. 856-867.

Zorman; "Silico Carbide as a Material for Biomedical Microsystems"; HAL archives-ouvertes.fr; EDA Publishing Association, pp. 7, 2009, <hal-00395712>; https://hal.archives-ouvertes.fr/hal-00395712; Jun. 16, 2009; 8 pgs.

* cited by examiner

Fig. 16

STEP 1

Spin coat and cure a polyimide release layer, about 1 micron thick, on a silicon wafer.

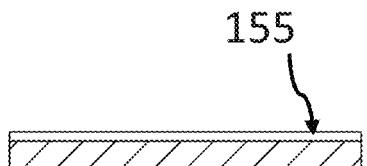

STEP 2

Deposit a first amorphous SiC layer with a thickness of about 2 microns over the polyimide release layer of Step 1 using Plasma Enhanced Chemical Vapor Deposition

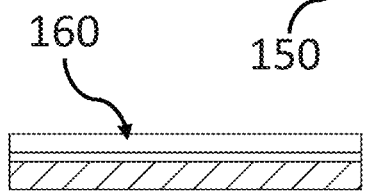

STEP 3

Deposit a patterned metal layer comprising titanium and gold thin films over the first amorphous SiC layer using sputter deposition and photolithography

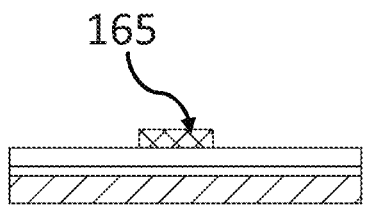

STEP 4

Deposit a second amorphous SiC layer with a thickness of about 2 microns over the patterned metal layer and first amorphous silicon carbide layer using Plasma Enhanced Chemical Vapor Deposition

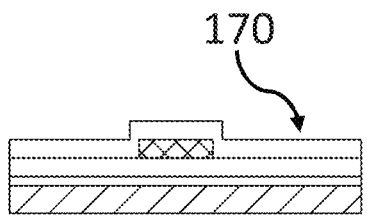

STEP 5

Form openings in the second amorphous SiC layer by reactive ion etching to define interface pads and electrical contact pads using photolithography to establish the location, shape and size of the pads

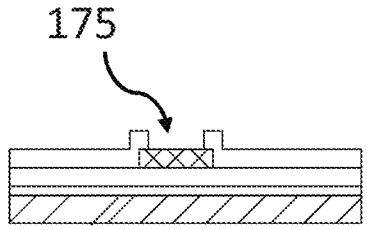

STEP 6

Define the external shape of the implantable body using reactive ion etching and photolithography

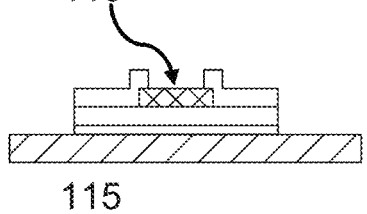

STEP 7

Silicon substrate and implantable devices are soaked in water to allow removal of the devices from the silicon wafer

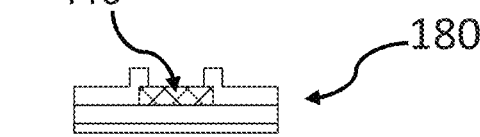

NEURAL INTERFACE DEVICE MANUFACTURING METHOD

CROSS-REFERENCE TO RELATED APPLICATION

This application is a divisional of U.S. application Ser. No. 16/015,878, filed Jun. 22, 2018, which claims benefit of U.S. Provisional Application Ser. No. 62/523,825, filed by Gardner, et al. on Jun. 23, 2017, entitled "NEURAL INTERFACE PROBE WITH AMORPHOUS SILICON CARBIDE INSULATION," commonly assigned with this application and incorporated herein by reference

GOVERNMENT LICENSE RIGHTS

This invention was made with Government Support under Contract No. NS090454 awarded by the National Institutes of Health. The government has certain rights in this invention.

TECHNICAL FIELD

This application is directed, in general, to a neural interface device and, more specifically, to an implantable body of the device and methods of manufacturing the same.

BACKGROUND

Chronically implanted microelectrode arrays (MEAs) for recording extracellular neural activity are central to scientific studies of neural circuit function. In clinical applications employing brain-machine and brain-computer interfaces such MEAs are essential for recording electrical neural signals. Limitations to achieving chronically stable neural recordings with existing microelectrode arrays include reactive tissue foreign body response that encapsulates the electrodes and kills or damages neurons, and, a decline in device performance often characterized by a progressive decrease in neural signal amplitude and loss of viable recording channels. Likewise, chronically implanted MEAs are employed in clinical applications requiring the delivery of therapeutic electrical stimulation. Such stimulating MEAs have the same limitations as recording MEAs.

SUMMARY

One embodiment of the invention is a neural interface device that comprises an implantable microelectrode body. The implantable microelectrode body includes a neural interface probe, which includes a thin film metal trace connected to an interface pad and an amorphous silicon carbide insulation. The amorphous silicon carbide insulation surrounds the thin film metal trace to form an outside surface of the neural interface probe. The interface pad is exposed to an ambient environment of the neural interface probe through an opening in the amorphous silicon carbide insulation.

Any such embodiments of the neural interface probe can have a rectangular cuboid shape, and a cross-sectional area perpendicularly transverse to a long axis length of the probe and through any perpendicularly transverse cross-section along the long axis length can be less than about 50 microns$^2$. For any such embodiments of the neural interface probe, the amorphous silicon carbide insulation can be the principle material of construction of the probe such that at least about 85 percent of a total area any one of the cross-sections along the long axis length is composed of the amorphous silicon carbide insulation.

Any such embodiments of the neural interface probe can have a buckling resistance of least about 15 N-µm$^2$. Embodiments of the neural interface probe can have a height and a breadth defining the cross-sectional area that provides the probe with a minimum area-moment-of-inertia of the cross-section of at least about 50 µm$^4$. In some such embodiments, at least one of the height or the breadth has a maximum value of about 20 µm, and preferably a maximum value of 10 □m. For any such embodiments of the neural interface probe, any one of the perpendicularly transverse cross-sections along the long axis length can have a total cross-sectional area of about 100 µm$^2$ or less. For any such embodiments of the neural interface probe, for the perpendicularly transverse cross-sections intersecting the thin film metal trace or the interface pad, a ratio of a cross-sectional area of the thin film metal trace to a cross-sectional area of the amorphous silicon carbide insulation is a value in a range from about 1:40 to about 10:40, and in some embodiments, in a range from about 1:40 to less than 4:40, and in some embodiments from about 1:40 to about 2:40.

For any such embodiments, the thin film metal trace can include one or more discrete layers composed of titanium, chromium, tungsten, gold, iridium, platinum, or palladium and the interface pad can include titanium nitride, iridium oxide, porous platinum, or poly(ethylenedioxythiophene). In some embodiments, the metal layers are partially intermixed to improve adhesion. For any such embodiments, the amorphous silicon carbide insulation of the probe can have an elastic modulus of about 300 GPa. For any such embodiments, the neural interface probe can consist essentially of the thin film metal trace the interface pad, and the amorphous silicon carbide insulation.

Any such embodiments of the implantable microelectrode body can further include a connection body surrounded by the amorphous silicon carbide insulation. The thin film metal trace of the neural interface probe can extend to a communication circuit of the connection body, and, the communication circuit can include an electrical contact pad directly connected to the thin film metal trace. In some such embodiments, the electrical contact pad can be connected, by a second opening in the amorphous silicon carbide insulation, to a wire lead or to a metal trace on a flexible ribbon cable to carry electrical signals via the wire lead or flexible ribbon cable between the interface pad and a non-implanted recording or stimulating apparatus of the device. In some such embodiments, the electrical contact pad can be connected to a telemetry unit of the device. The telemetry unit can be configured to wirelessly carry electrical signals between the interface pad and a non-implanted recording or stimulating apparatus of the device.

For any such embodiments of the implantable microelectrode body the amorphous silicon carbide insulation can include a first amorphous silicon carbide layer and a second amorphous silicon carbide layer. The thin film metal and the interface pad can lay on the first amorphous silicon carbide layer and the second amorphous silicon carbide layer can cover the thin film metal and some or all of the first amorphous silicon carbide layer. The opening in the amorphous silicon carbide insulation can be through the second amorphous silicon carbide layer to thereby expose the interface pad to the ambient environment. For some such embodiments, the neural interface probe can further include a second thin film metal trace connected to a second interface pad.

For some such embodiments, the second thin film metal trace and the second interface pad can be located on the first amorphous silicon carbide layer and the second amorphous silicon carbide layer can cover the thin film metal and some or all of the first amorphous silicon carbide layer. The second thin film metal trace and the second interface pad can be laterally separated from the first thin film trace and the first interface pad that are located on the first amorphous silicon carbide layer. The opening in the amorphous silicon carbide insulation can include discrete openings through the second amorphous silicon carbide layer to thereby expose the first interface pad and the second interface pad to the ambient environment.

Additionally or alternatively, for some such embodiments, the second thin film metal trace and the second interface pad can be located on the second amorphous silicon carbide layer and a third amorphous silicon carbide layer of the amorphous silicon carbide insulation can cover the second thin film metal trace. The second thin film metal trace and the second interface pad can be laterally and vertically separated from the thin film trace and the interface pad located on the first amorphous silicon carbide layer. The opening in the amorphous silicon carbide insulation can include discrete openings through the second amorphous silicon carbide layer and through the third amorphous silicon carbide layer to thereby expose the first interface pad and the second interface pad to the ambient environment.

Any embodiments of the neural interface probe can further include a plurality of thin film metal traces located on any of a plurality of amorphous silicon carbide layers. At least one of the thin metal traces is exposed to the ambient environment through an opening in one or more of the amorphous silicon carbide layers.

Any embodiments of the implantable microelectrode body can further include a plurality of the neural interface probes.

Another embodiment of the present invention is a method of manufacturing the neural interface device that comprises forming a neural interface probe of an implantable microelectrode body. Forming the neural interface probe can include plasma enhanced chemical vapor deposition of a first amorphous silicon carbide insulation layer, and forming a thin film metal trace and interface pad on the first amorphous silicon carbide insulation layer, wherein the interface pad is formed on a portion of the thin film metal trace. Forming the neural interface probe can include plasma enhanced chemical vapor deposition of a second amorphous silicon carbide insulation layer on the first amorphous silicon carbide insulation layer and covering the thin film metal trace and the interface pad, and forming an opening in the second amorphous silicon carbide insulation layer to expose the interface pad to an ambient environment. Forming the neural interface probe can include patterning the first and second amorphous silicon carbide insulation layer to define the neural interface probe, including any of the embodiments of the neural interface probe of the above-disclosed neural interface device.

In any such embodiments of the method, the plasma enhanced chemical vapor deposition conditions of the first and second amorphous silicon carbide insulation layers and the formation conditions of the thin film metal trace and the interface pad can be selected such that intrinsic stresses in the first and second amorphous silicon carbide insulation layers are offset by residual stresses in the thin film metal trace and the interface pad, such that the neural interface probe has a substantially neutral stress. In some such embodiments, the plasma enhanced chemical vapor deposition conditions of the first and second amorphous silicon carbide insulation layers includes a temperature in a range from about 200 to about 400° C., a deposition pressure in a range from about 800 to about 1200 millitorr, a reactive gas mixture comprised of silane ($SiH_4$) and methane ($CH_4$), with a molar compositional ratio ($SiH_4$:$CH_4$) in a range from about 1:2 to about 2:1, a carrier gas of argon, and a total flow rate of the reactive gas mixture plus the carrier gas in a range from about 600 to about 1200 sccm. In some such embodiments, the formation conditions of the thin film metal trace and the interface pad includes a physical vapor deposition process that can include sputtering with an inert gas plasma at a pressure in a range from about 1 and 40 about millitorr, or, thermal evaporation at an ambient deposition temperature. In some such embodiments, each of the first and the second amorphous silicon carbide insulation layers can have a thickness in a range from about 0.1 to about 4 microns, and each of the first and the second amorphous silicon carbide insulation layers can have a compressive residual stress in a range from about 50 to about 200 MPa. In some such embodiments, the thin metal trace can have a thickness in a range from about 0.1 and about 2 microns, and the thin metal traces can have a residual stress in a range from about 100 MPa in compression to about 500 MPa in tension.

BRIEF DESCRIPTION

Reference is now made to the following descriptions taken in conjunction with the accompanying drawings, in which:

FIG. 1 is a plan view of an example embodiment of a microelectrode body (100) comprising a neural interface probe (105), a thin film metal trace (110), an interface pad (115) defined by a first opening in an amorphous silicon carbide layer (135), a connection body (120), an electrical contact pad (125) defined by a second opening in the amorphous silicon carbide, and a distal tip (130) at the terminus of the neural interface probe (105) defined by an included angle of less than 90 degrees);

Figure 9:
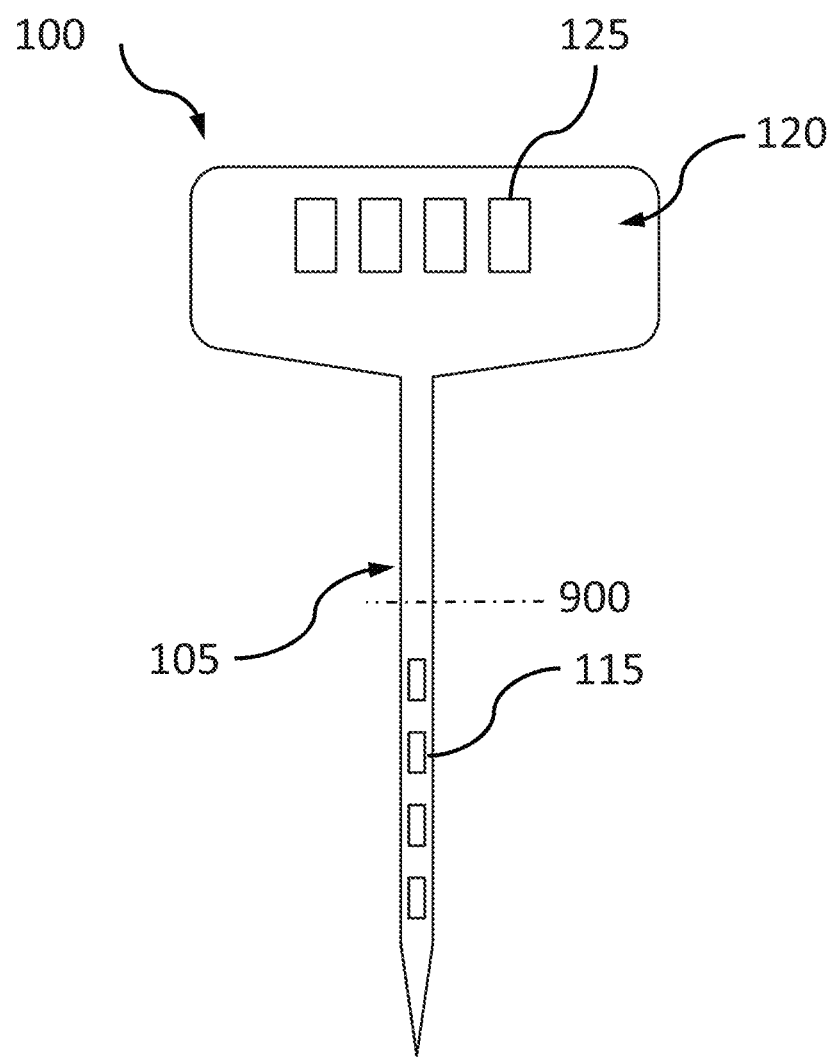
Figure 10:
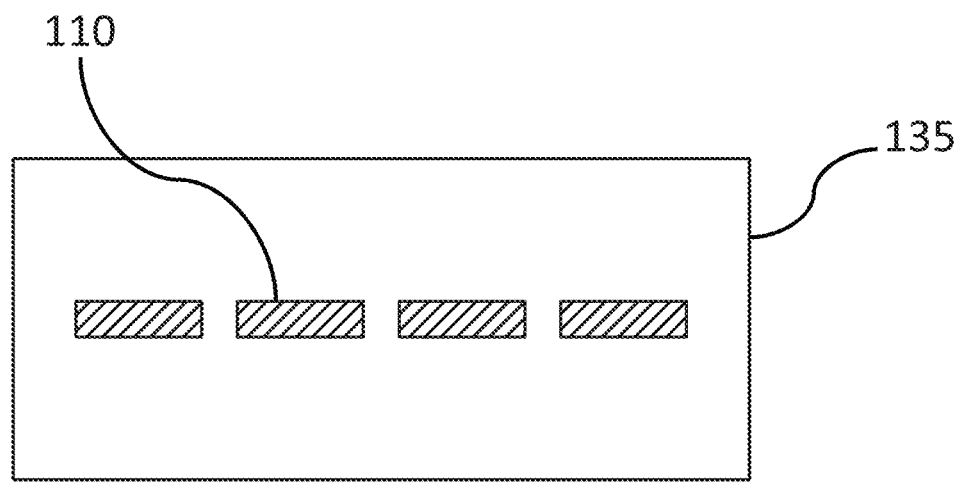
Figure 11:
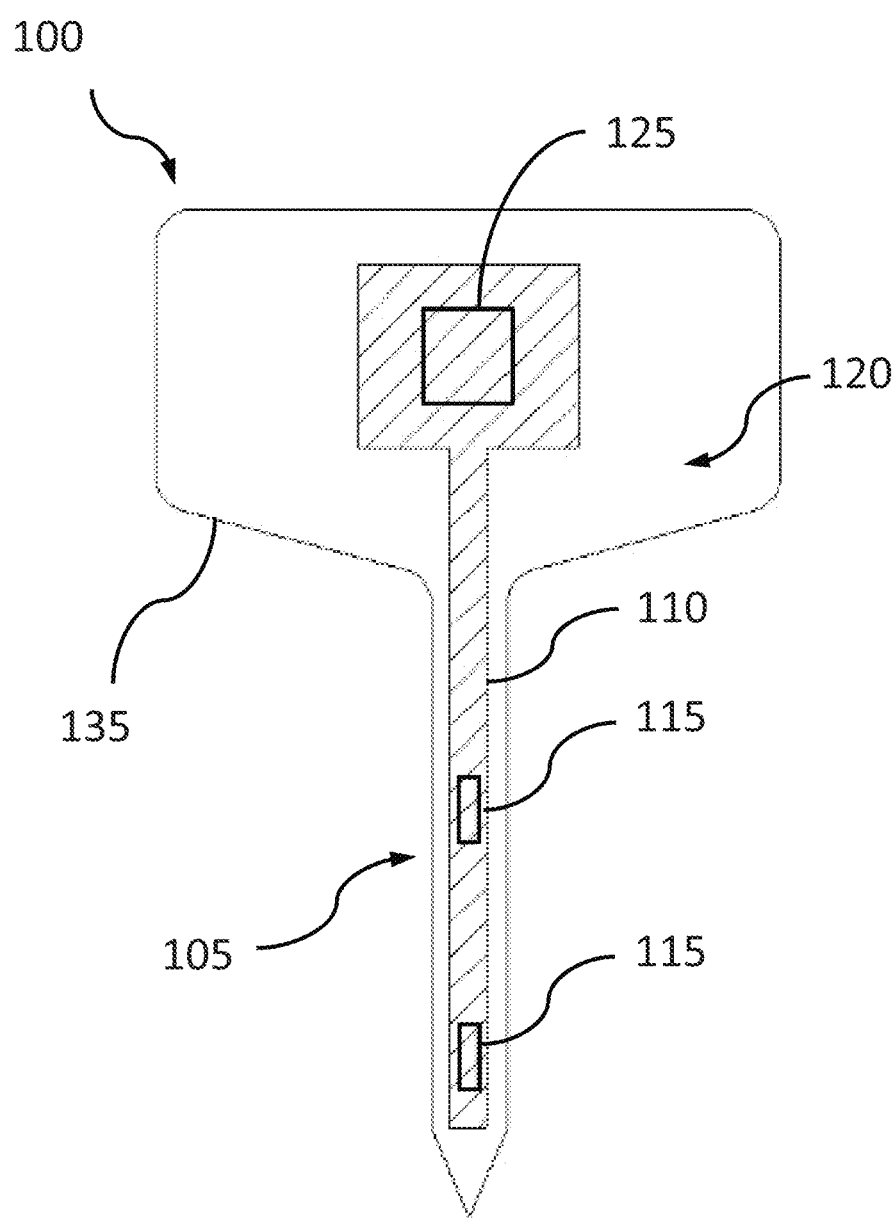

FIG. 9 shows an example embodiment of the implantable microelectrode body (100) wherein an interface probe (105) is configured to have a plurality of neural interface pads (115) defined by a first set openings in an a-SiC layer (120), the interface pads in contact with one or a plurality of metal traces (for clarity not shown) in contact with a plurality of electrical contact pads (125) defined by a second set of openings in an a-SiC layer (120);

FIG. 10 is an example embodiment related to the implantable microelectrode body (100) described FIG. 9, showing a perpendicular cross section located at (900) of the neural interface probe (105) having thin film metal traces (110) completely surrounding by a-SiC (135);

FIG. 11 is an example embodiment of the implantable microelectrode body of the present invention (100) having a plurality of interface pads (115) defined by a first set of openings in an a-SiC layer (135) wherein the interface pads are in contact with at least one fewer thin film metal traces (110), the thin film metal traces extending to a connection body (120) having electrical contact pads (125) defined by a second set of openings in an a-SiC layer (135).

Figure 12:
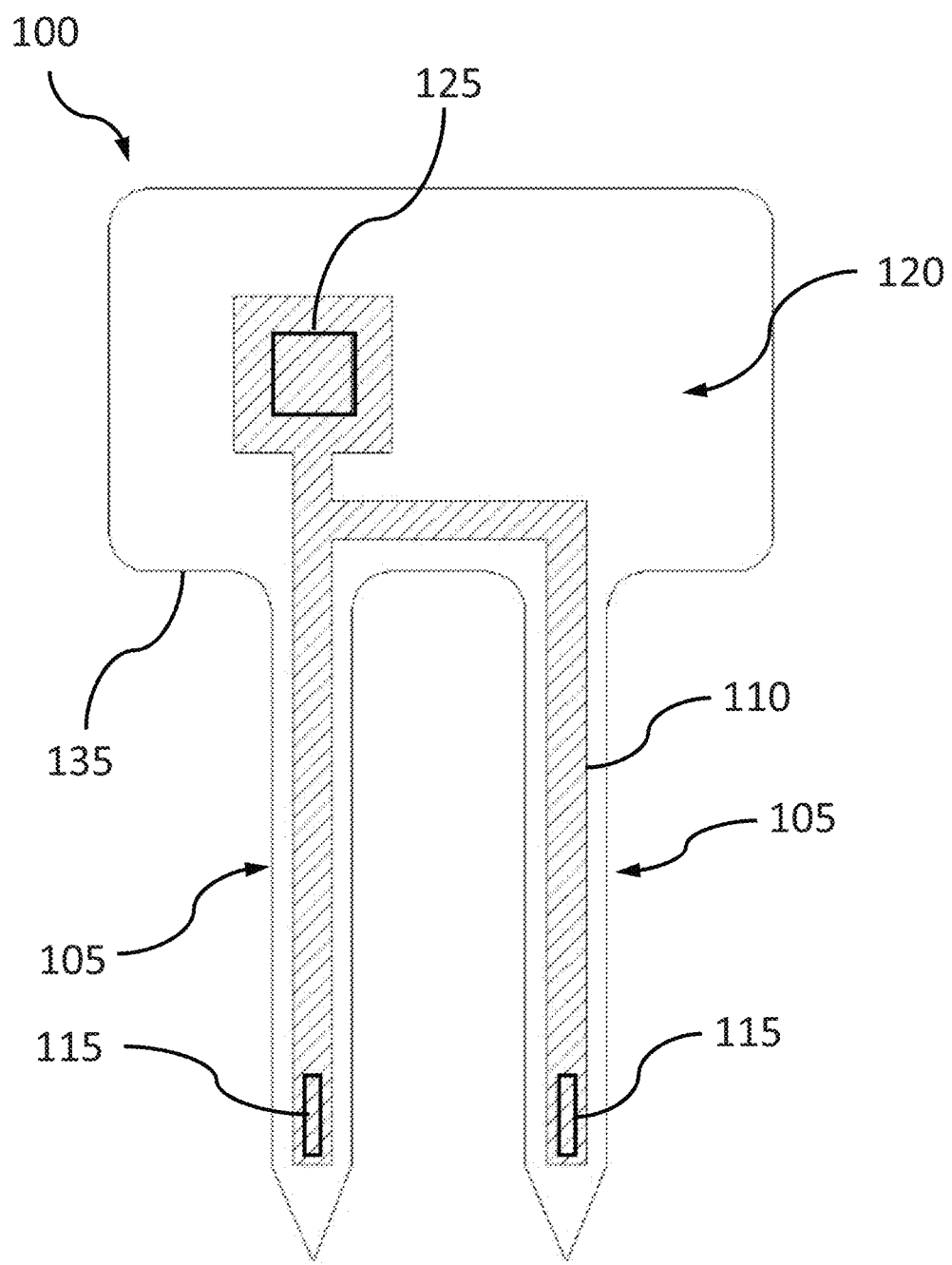

FIG. 12 is an example embodiment of the implantable microelectrode body of the present invention (100) having a plurality of neural interface probes (105) in contact with a connection body (120), the neural interface probes having interface pads (115) defined by a first set of openings in an a-SiC layer (135), the interface pads being in contact with at least one fewer thin film metal traces (110), a least one thin film metal trace being disposed on a plurality of neural interface probes, the thin film metal traces extending to a connection body (120) having electrical contact pads (125) defied by a second set of openings in an a-SiC layer (135).

Figure 13:
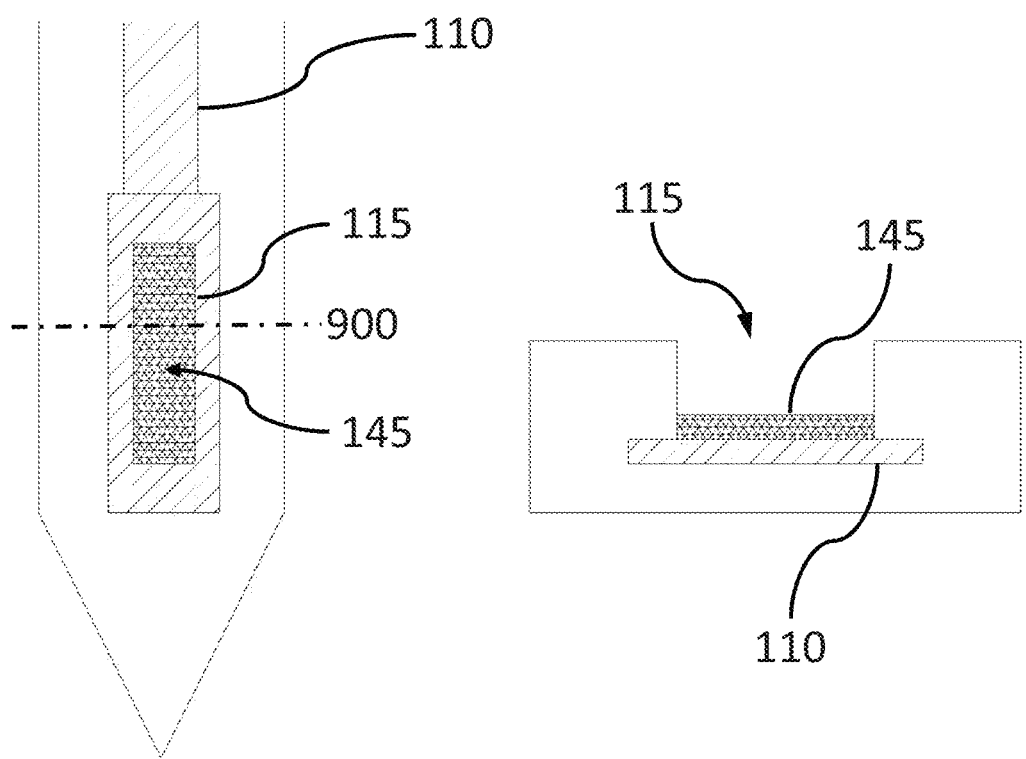
Figure 14:
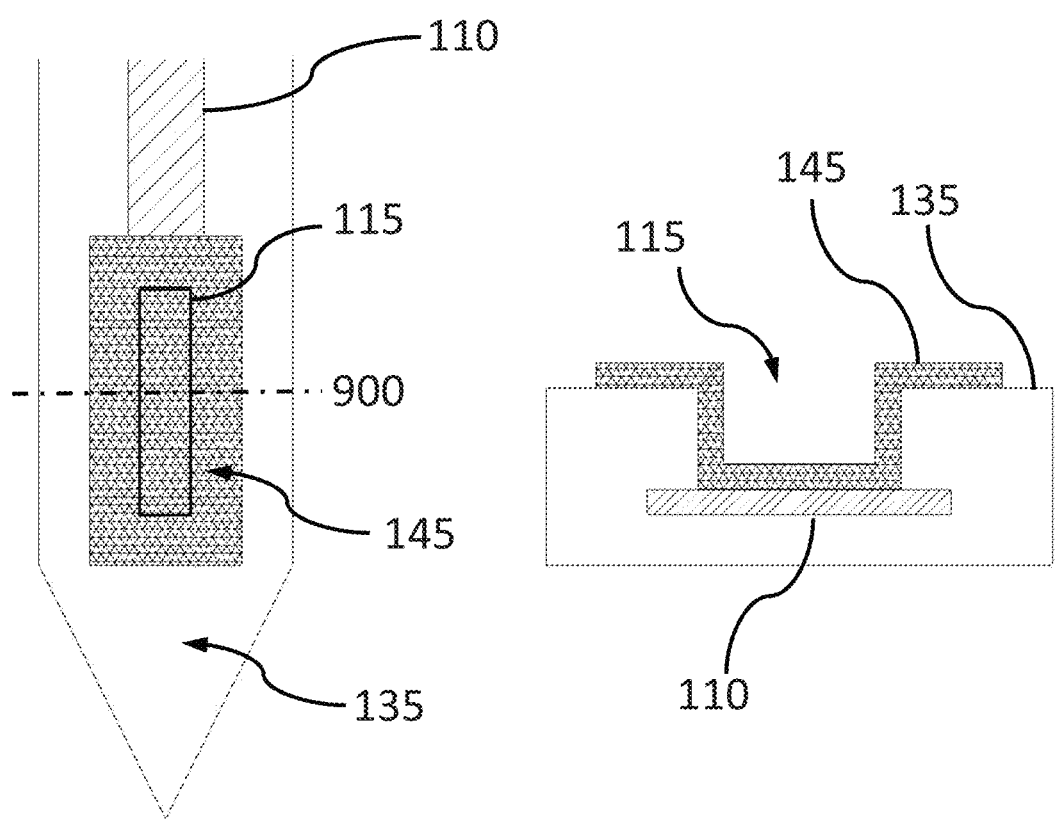
Figure 15:
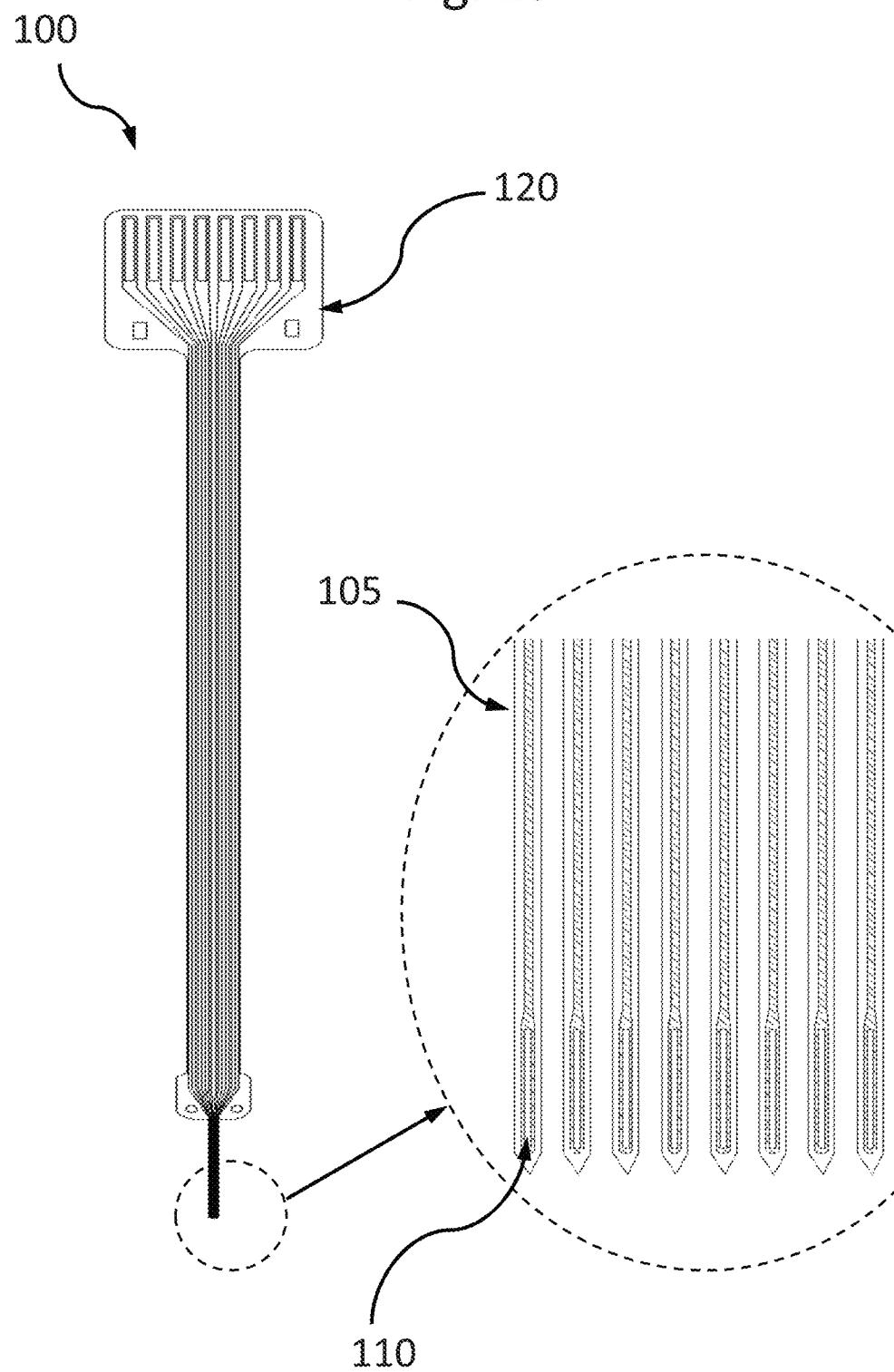
Figure 17:
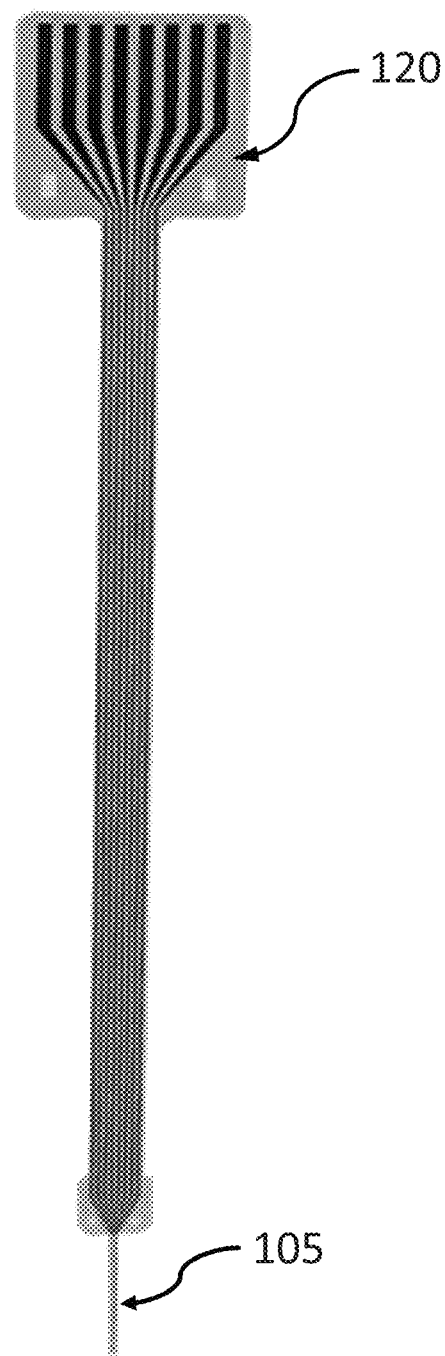
Figure 18:
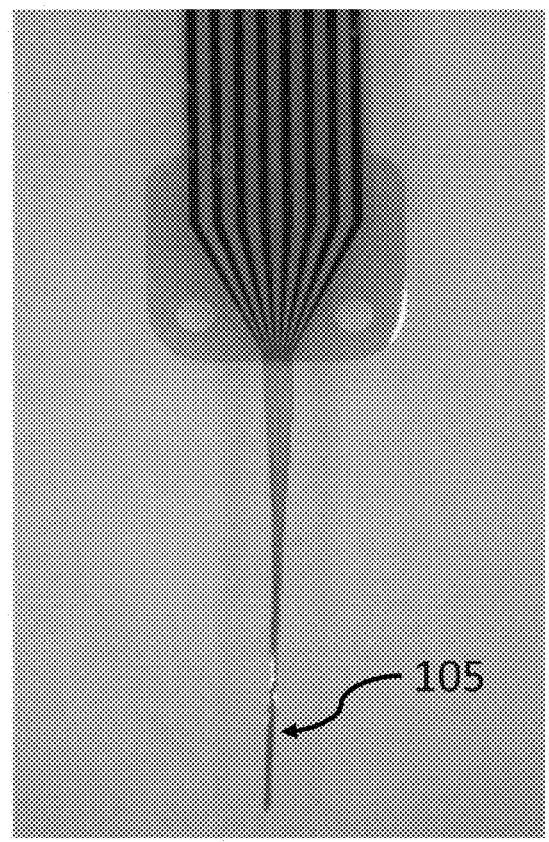
Figure 19:
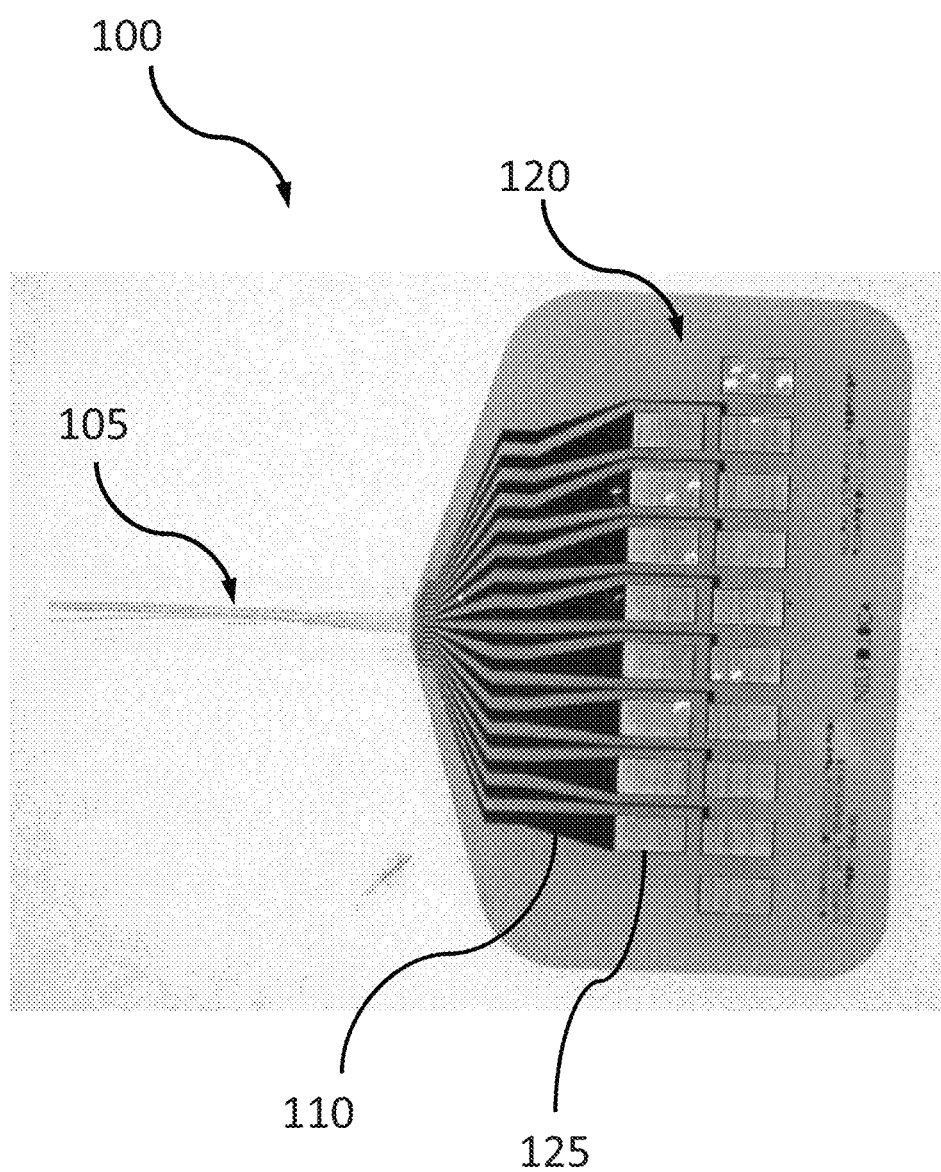
Figure 20:
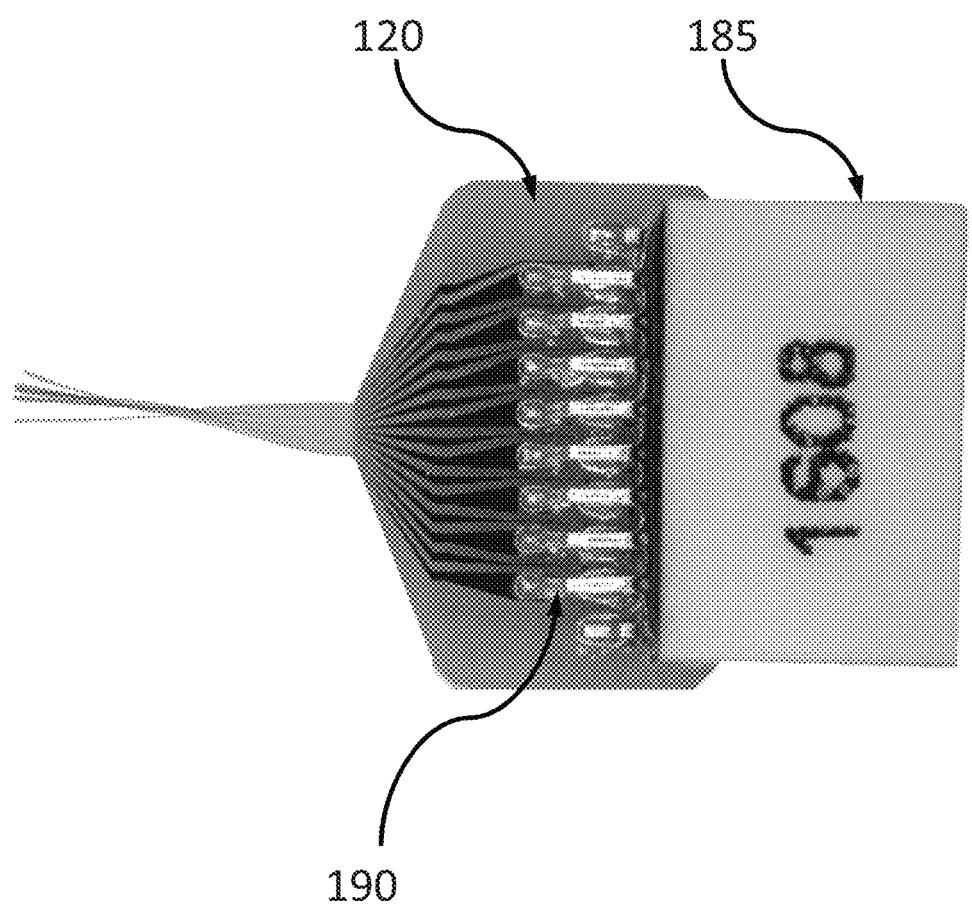
Figure 21:
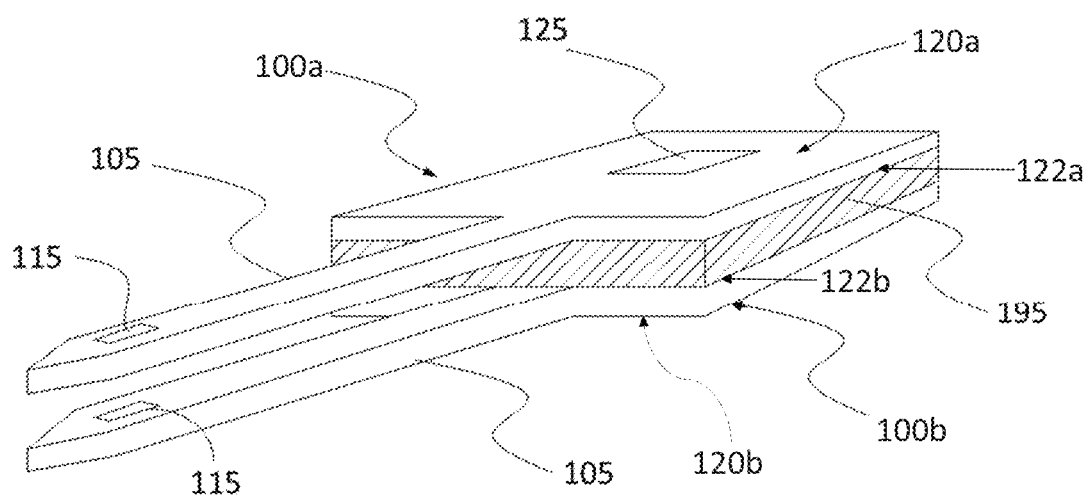

FIG. 13 shows a plan view and a perpendicular cross-sectional view located at (900) of an example embodiment of the invention wherein an interface pad (115) is coated with an electrode material (145), a first surface of the electrode material in contact with a thin film metal trace (110) and a second surface of the electrode material in contact with the ambient;

FIG. 14 shows a plan view and a perpendicular cross-sectional view located at (900) of an example embodiment of the invention wherein an interface pad (115) is coated with an electrode material (145), a first surface of the electrode material in contact with a thin film metal trace (110) and with a surface of the a-SiC (135) and a second surface of the electrode material in contact with the ambient;

FIG. 15 is an example embodiment of a neural microelectrode body (100) having eight neural interface probes (105), each neural interface probe having an interface pad (110) in contact with a metal trace (110), the metal trace extending to a distant connection body (120);

FIG. 16 is a diagrammatic overview of the fabrication of an embodiment of the present invention;

FIG. 17 is an optical photograph of an example embodiment of an implantable microelectrode body showing a separation between neural interface probes (105) and a connection body (120);

FIG. 18 is a magnified optical image of the distal end of the implantable microelectrode body showing bundling of neural interface probes (105) to form a monolithic structure with increased resistance to buckling during implantation;

FIG. 19 is a magnified optical image of an embodiment of the present invention having neural interface probes (105) with a length of about 4 mm suitable for implantation into brain;

FIG. 20 is a magnified optical image of the embodiment shown in FIG. 19, further configured with an electrical connector (185) attached to electrical contact pads on the connection body (120) using solder joints (190); and FIG. 21 is an embodiment of the present invention showing a plurality of neural interface devices (100) in a stacked arrangement, wherein the individual neural interface devices are separated by a spacer (195) to form a monolithic structure useful for interfacing with a three-dimensional volume of tissue.

DETAILED DESCRIPTION

As part of the present invention is our recognition that neural interface probes whose principle material of construction is composed of amorphous silicon carbide (a-SiC) insulation possess several desirable characteristics. Making such probes principally out of a-SiC allows the manufacture of a probe with a small enough cross-sectional area to minimize foreign body response, but still provide enough buckling resistance to reduce undesirable buckling, when implanted into tissue. Additionally, providing a probe whose outer surface is substantially entirely composed a-SiC (e.g., at least about 90 percent of the outer surface) provides an excellent barrier against biological fluids that could corrode metal thin film traces of the probe and cause a decline in device performance.

The neural interface devices of the present invention employ amorphous silicon carbide. Amorphous silicon carbide is distinguished from other forms of silicon carbide by not exhibiting crystallinity when analyzed by x-ray diffraction. Prior art devices discloses the use of polycrystalline silicon carbide in the construction of devices intended for interfacing to neural tissue. Diaz-Botia et al., 2017 teach the use of crystalline silicon carbide in a geometry that disposes electrode sites in a planar configuration on the surface of a neural tissue target. Polycrystalline silicon carbide is formed at high temperatures by low pressure chemical vapor deposition and is n-doped and consequently has electronic conductivity. The high deposition temperature and electronic conductivity make n-type silicon carbide unsuitable for fabrication of the neural interface probes of the present invention. Frewin et al., (WO 2013/010161 A2) disclose a long-term implantable neural interface device employing crystalline silicon carbide (3C-SiC) wherein the cubic silicon carbide is employed as a base material in an electrolyte insulator semiconductor capacitor and as a base material in a field effect transistor. Diaz-Botia et al., 2017, employ amorphous silicon carbide as an insulating encapsulation layer for metal traces in their neural interface probes. Similarly, Lei et al., 2016 describe the use of amorphous silicon carbide as a protective coating for neural interface devices placed in contact with retinal neural tissue; Cogan et al., 2003 describe the use of amorphous silicon carbide as an insulating coating for microelectrodes that are implanted into neural tissue; and Cogan, U.S. Pat. No. 5,755,759 describes the use of amorphous silicon carbide in combination with amorphous silicon oxycarbide as a high electronic resistivity coating for a neural interface probe. None of the aforementioned Prior Art references describe the use of amorphous silicon carbide as the predominant material of construction of an neural interface probe and, further, do not describe neural interface probes employing amorphous silicon carbide in a geometry that advantageously allows the implantation of neural interface probes into neural tissue, or other tissues, wherein the neural interface probes have a geometry that substantial avoids an adverse foreign body response.

Figure 1:
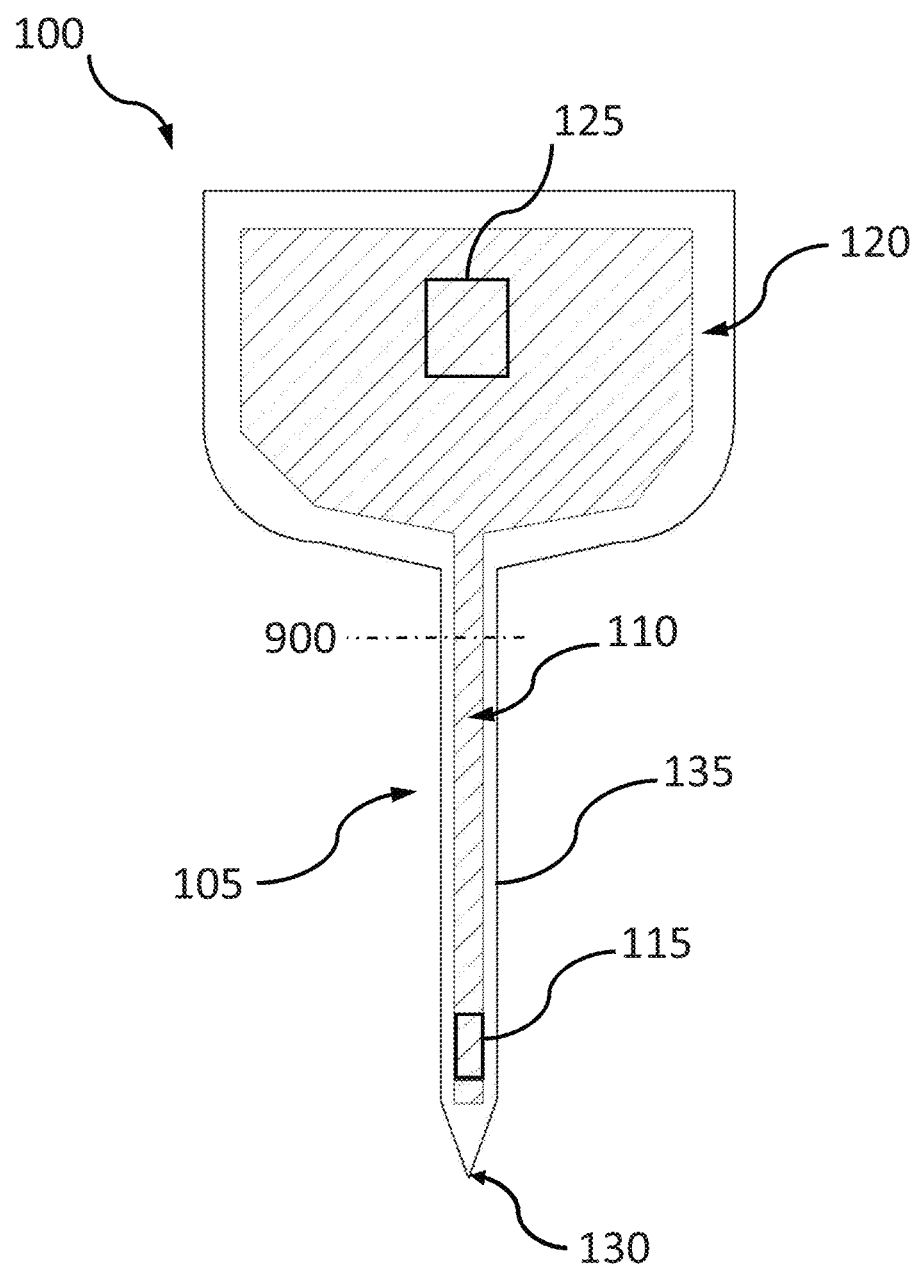
Figure 2:
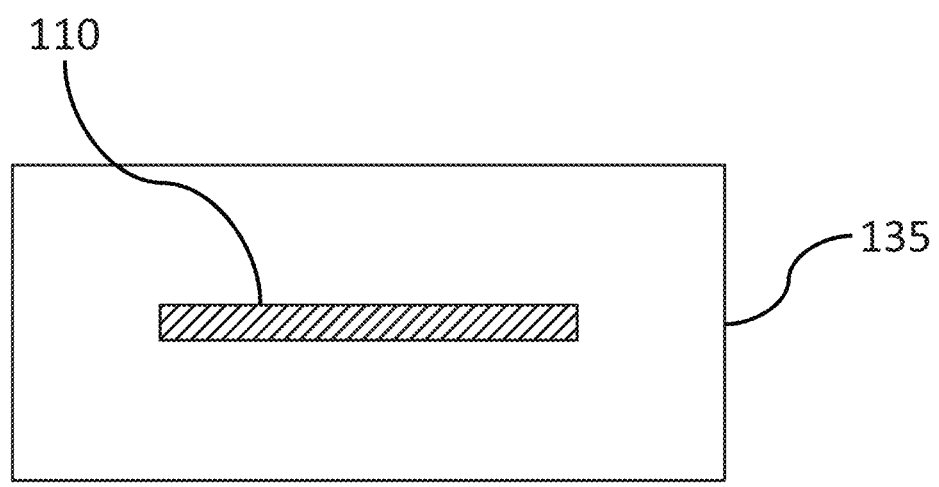
FIG. 2 is a perpendicular cross-sectional view of the neural interface probe (105) of FIG. 1 and taken at the section indicated in FIG. 1 (900) showing a thin film metal trace (110) completely surrounding by a-SiC (135)

One embodiment of the disclosure is a neural interface device. FIG. 1 presents a plan view of an example embodiment of the device (100). The device comprises a neural interface probe (105) which is implanted into the neural tissue from which neural electrical activity is recorded or neural activity electrically stimulated. An interface pad (115) is defined on the neural interface probe by an opening in an a-SiC layer (135). The interface pad has the property of being electronically conducting and provides an electrical connection to the neural tissue of the ambient environment. The length of the neural interface probe and the position of the interface pad along the longitudinal axis of the neural interface probe are chosen to place the interface pad at a location in the ambient advantageous for neural recording and stimulation. To facilitate the implantation of the neural interface probe into tissue, the distal tip (130) of the probe is configured with a point capable of penetrating into tissue with minimal force. In one embodiment, the distal tip is defined by two rectangular sides of the neural interface probe that intersect at the distal tip with an included angle of 90 degrees or less. In a related embodiment, the distal tip may be configured to have a radius of curvature. The radius of curvature is less than or equal to one half the width of the neural interface probe. It is possible to combine these embodiments. The thin film metal trace (110) extends from the interface pad to a connection body (120). Electrical connection to the implantable microelectrode device can be made at the connection body by creating an opening in an a-SiC layer to form an electrical contact pad (125).

The term rectangular cuboid shape as used herein refers to a substantially box-shaped structure defined in three dimensional space by a length (corresponding to the long axis), a breadth (corresponding to the horizontal width) and height (corresponding to the thickness) of the probe with the exception in some embodiments of the insertion end of the probe which can be tapered to facilitate tissue insertion. The faces of the rectangular cuboid shaped probe are substantially planar.

The term amorphous silicon carbide refers to a silicon carbide structure that is substantially devoid of crystal structures such as indicated by an x-ray diffraction scan that would not show discrete sharp peaks of scattered radiation corresponding to crystalline or crystallite forms of silicon carbide. For example, substantially the entire (e.g., at least about 99% percent) x-ray diffraction spectrum of an a-SiC structure of the disclosure may have no x-ray diffraction peaks with a full width at half maximum of less than about 5 degrees in diffraction angle.

In an embodiment of the invention directed to facilitating the implantation of amorphous silicon carbide neural interface probes into tissue, the neural interface probe is configured to resist buckling as it traverses through tissue. While enabling passage of the probe through tissue, the configuration advantageously preserves cross-sectional dimensions of the probe that minimize insertion trauma and foreign body response. The desirable properties of buckling resistance and minimizing foreign body response present conflicting requirements on the cross-sectional dimensions and stiffness of a neural interface probe. Buckling resistance may be achieved by increasing cross-sectional dimensions of the neural interface probe whereas minimizing insertion trauma and foreign body response may be achieved by decreasing the cross-sectional dimensions of the neural interface probe. Without regard to the length of the neural interface probe, the buckling resistance of a probe is proportional to the elastic modulus (E) of the probe in its longitudinal dimension multiplied by the smallest area-moment-of-inertia of the probe cross-section (I). In the present embodiment, the probe is configured with an approximately rectangular cross-section with base dimension b and height dimension h, the height dimension h being less than or equal to the base dimension b. The smallest area-moment-of-inertia is then given by the well-known formula, $$I = \frac{bh^3}{12}$$

To minimize insertion trauma and the foreign body response, it is desirable to a have at least one cross-sectional dimension of the probe less than 10 micrometers. Thus, for a neural probe of approximately rectangular cross-section, h is desirably less than 10 micrometers. Skilled artisans will understand that the fabrication of thin films devices comprising multiple patterned layers often results in cross-sectional geometries that are often trapezoidal. A rectangular cross sectional geometry is used for illustration without limitation.

An advantage of the rectangular cross-section compared with the circular cross-section employed in Prior Art carbon fiber electrodes is the higher area moment of inertia of the rectangular cross-section for the same minimum cross-sectional dimension. By way of example, a rectangular neural interface probe with h=5 micrometers has a minimum area moment of inertia of 52 $\square m^4$ when b=5 micrometers. A circular neural probe with an equivalent minimum cross-sectional dimension has an area moment of inertia of 31 $\square m^4$. Thus for a fixed minimum cross-sectional dimension, the area moment of inertia of the rectangular cross-section is higher, imparting the desirable property of increased buckling resistance. Likewise, comparing a neural probe with a rectangular cross-section with a probe having a circular cross-section, both having the same area moment of inertia, the rectangular probe has a minimum cross-sectional dimension that is less than or equal to 88% that of the circular probe. The smaller cross-sectional dimension of the rectangular probe advantageously reduces the foreign body response.

The foregoing discussion teaches an advantage of a neural probe with a rectangular cross section for increasing buckling resistance while minimizing tissue damage. A further increase in buckling resistance is obtained by configuring the cross-section of the probe to comprise substantially of a high-elastic-modulus material. A further advantage is obtained if the high elastic modulus material is disposed on the perimeter of the probe cross-section. The present invention is directed to the use of amorphous silicon carbide as the high elastic modulus material. Amorphous silicon carbide has a modulus of elasticity of approximately 300 GPa. Skilled artisans will appreciate that the modulus may vary depending on the method and process parameters used in the preparation of the amorphous silicon carbide. Since the buckling resistance is proportional to the EI product, an amorphous silicon carbide probe with a rectangular cross section having dimensions b=h=5 micrometers will have a buckling resistance proportional to 15.6 N-$\square$m². In a preferred embodiment of the invention, therefore, the amorphous silicon carbide neural interface probe has an EI product of 15.6 N-$\square$m² or larger with at least one cross-sectional dimension less than 10 $\square$m. Skilled Artisans will understand that the contribution of the metal trace or traces within the neural interface probe may also influence the EI product. Metals used in the construction of the traces have a lower modulus of elasticity than amorphous silicon carbide, which has the effect of decreasing the EI product of the probe. Consequently, the cross-sectional dimensions of an interface probe having a multiplicity of metal traces may be increased to achieve a desired EI product while preserving the constraints that at least one cross-sectional probe dimension is less than 10 $\square$m and the EI product is 15.6 N-$\square$m² or greater.

A useful feature of the neural interface probe of the present invention is a high degree of planarity. Planarity is the property of the neural interface probe that the upper and lower surfaces of the probe are co-planar and that each of these surfaces lie within a plane. The planarity of the probe is advantageous in minimizing tissue damage during implantation. It is commonly understood that thin films of materials fabricated by the processes employed in the fabrication of the neural interface probes have intrinsic residual stresses. If these stresses are unbalanced or non-uniformly distributed within the neural interface probe, a deflection of the probe occurs with consequent loss of planarity. In amorphous silicon carbide these residual stresses are typically compressive. Carefully selection of deposition conditions for the formation of the amorphous silicon carbide is required to minimize these stresses. Advantageously for the fabrication of the neural interface probes, the amorphous silicon carbide has an intrinsic stress between −50 MPa and −150 MPa, where the minus sign indicates a compressive stress state. The metal traces used in the fabrication of the interface probes also contain residual stresses. An inventive feature of the neural interface probes is the control of residual stress within the metal traces and selection of the area-fraction of the metal within the probe cross-section to balance the compressive stress within the amorphous silicon carbide. Therefore, in an embodiment of the invention the metal traces have a tensile residual stress and are configured to have a cross-sectional area and position within the shank cross-section such that the bending moment about the neutral axis of the probe is minimized and sufficient planarity is retained to permit implantation into tissue.

Figure 3:
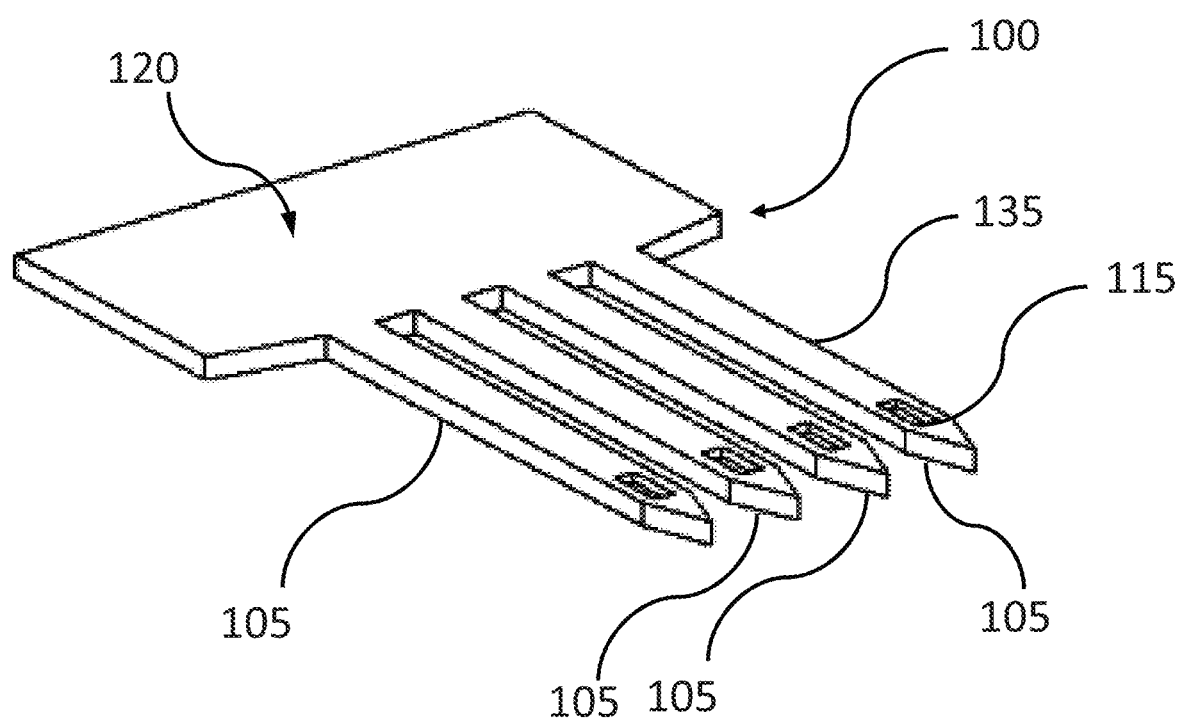
FIG. 3 is an embodiment of the implantable microelectrode body (100) comprising four neural interface probes (105) in contact with a connection body (120) wherein each neural interface probe is configured to have a neural interface pad (115) defined by an opening in an a-SiC layer (135)
Figure 4:
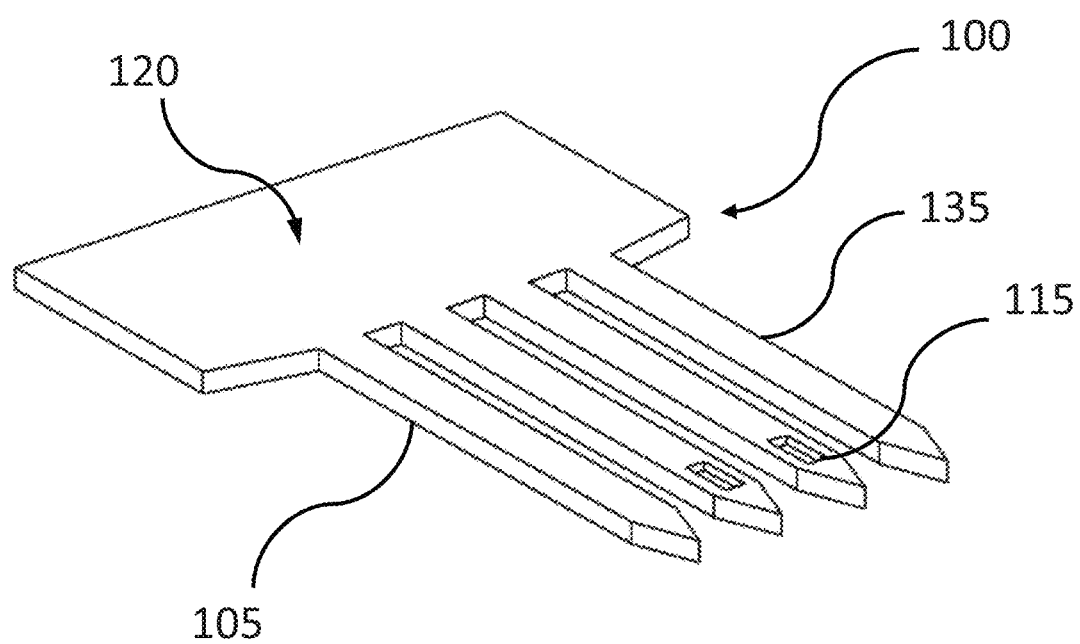
FIG. 4 is an embodiment of the implantable microelectrode body (100) comprising four neural interface probes (105) in contact with a connection body (120) wherein two neural interface probes are configured to have a neural interface pad (115) defined by an opening in an a-SiC layer (135)

As part of the present invention, it is recognized that an implantable microelectrode body with a plurality of neural interface probes has desirable characteristics. The plurality of interface probes increases the number of neural interface pads in contact with the ambient and allows control of the spatial distribution of the contact pads in the ambient. One embodiment of the present invention having a plurality of neural interface probes (105) is shown in perspective view in FIG. 3. The implantable microelectrode body (100) is shown with four neural interface probes. Typically, each neural interface probe will have one or a plurality neural interface pads (115) distributed along the longitudinal axis of the probe. In some aspects of the present embodiment (FIG. 4), one or more of the plurality of neural interface probes (105) is configured without a neural interface pad. Neural interface probes without a neural interface pad are desirable for the purpose of stabilizing an implantable microelectrode body on the surface of the implanted tissue.

Figure 5:
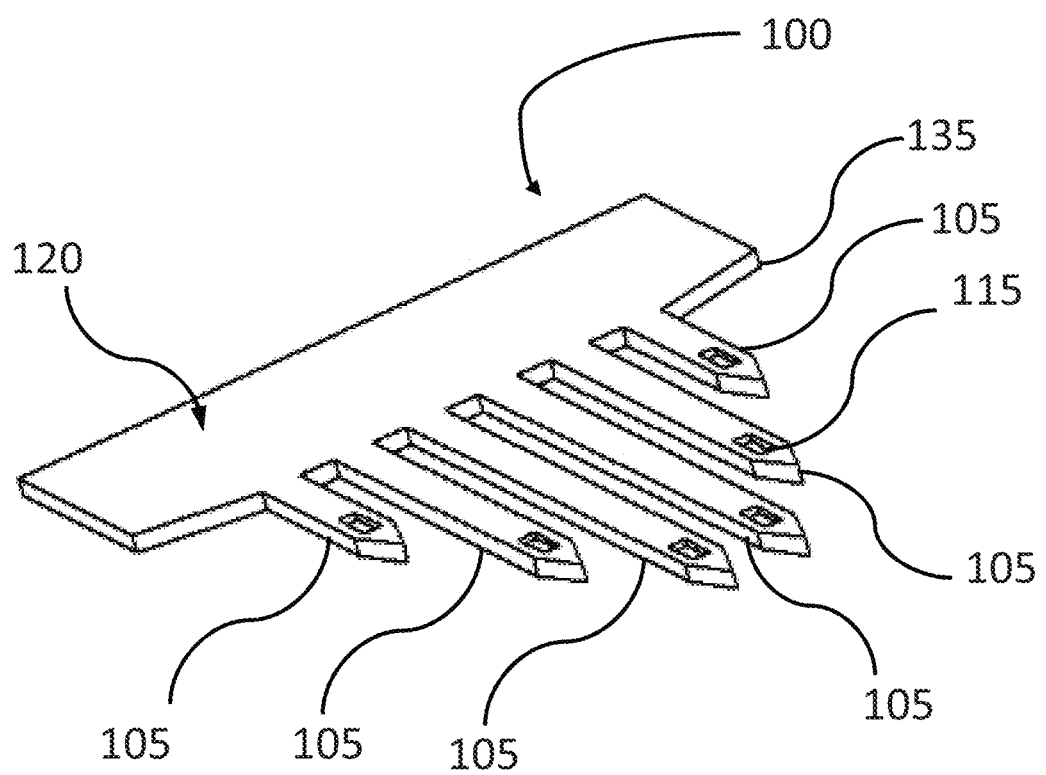
FIG. 5 is an embodiment of the implantable microelectrode body (100) comprising six neural interface probes (105) in contact with a connection body (120) wherein the neural interface probes are configured to have more than one length, each neural interface probe optionally having a neural interface pad (115) defined by an opening in an a-SiC layer (135)
Figure 6:
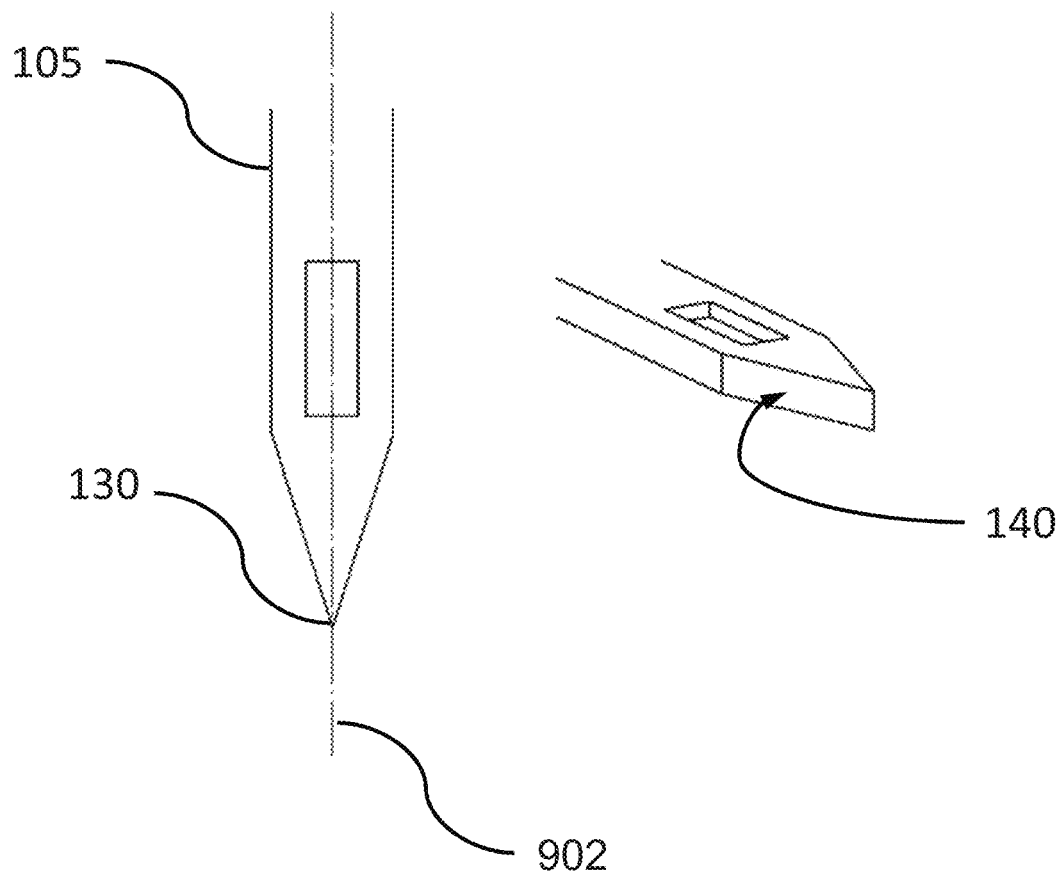
FIG. 6 is an embodiment of the invention showing a neural interface probe (105) with a distal tip (130) extended to a point symmetrically about a centrally positioned longitudinal axis (902) of the probe and defined by the convergence of two approximately rectangular sides (140) of the probe tip.

In a related embodiment of an implantable microelectrode device with a plurality of neural interface probes shown in FIG. 5, the longitudinal length of the individual neural interface probes is selected to favorably distribute the neural interface pads (115) over a range of depths in the ambient. Without limitation, advantageous lengths of the neural interface probes may range from about 0.05 mm to 20 mm. Neural interface probes with a length from 0.05 mm to about 4 mm are particularly suited to peripheral nerve implantation. Neural interface probes with a length from about 0.5 mm to 20 mm are particularly suited to cortical implantations and to implantation in deep brain structures.

In as aspect of the invention related to any embodiment, the distal tip (130) of a neural interface probe (105) has a geometry suitable for penetrating tissue. The distal tip is located at the terminus of the neural interface probe at its greatest distance from the connection body (120). A suitable geometry includes a distal tip defined by two approximately rectangular sides (140) of the neural interface probe that symmetrically converge about a center line (900) to a point with an included angle of less than about 90 degrees and more preferably less than about 20 degrees.

Figure 7:
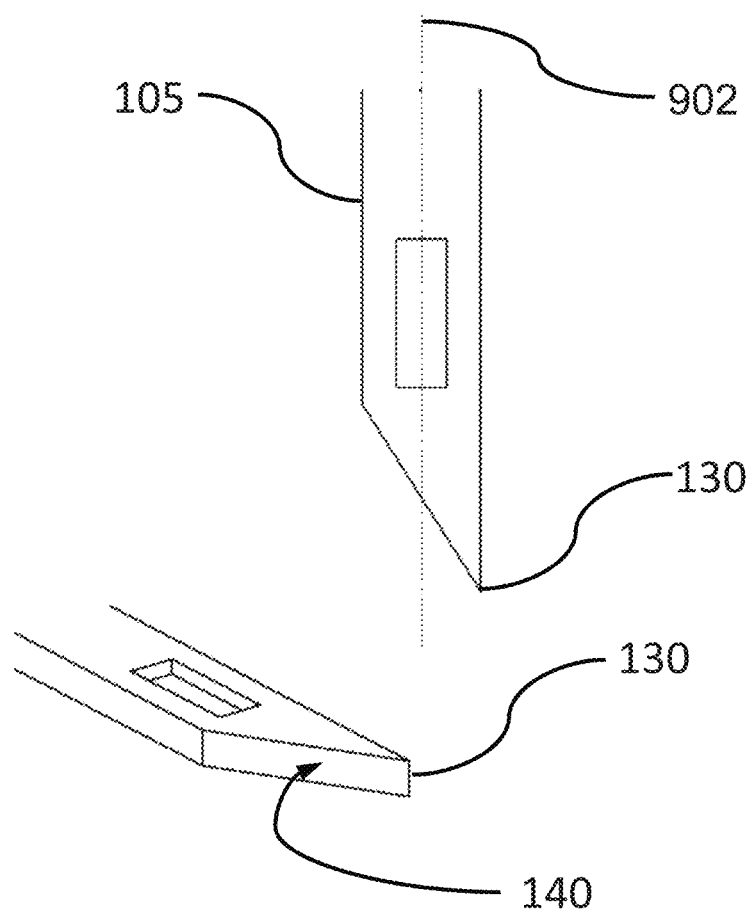
FIG. 7 is an embodiment of the invention showing a neural interface probe (105) with a distal tip (130) extended to a point asymmetrically about a centrally positioned longitudinal axis (902) of the probe and defined by the convergence of two approximately rectangular sides (140) of the probe tip.

In an aspect of the invention related to the geometry of the distal tip of a neural interface probe (105), the sides (140) of the neural interface probe at the distal tip converge asymmetrically as shown in FIG. 7. The included angle between the convergent sides remains less than 90 degrees and preferably less than 20 degrees. A tip that converges asymmetrically may be used advantageously to direct the path taken by the neural interface probe as it traverses through tissue during implantation. The neural interface probe is deflected in a direction opposite to the rectangular side of the neural interface probe tip presenting the largest surface area projected in the direction of motion of the probe.

Figure 8:
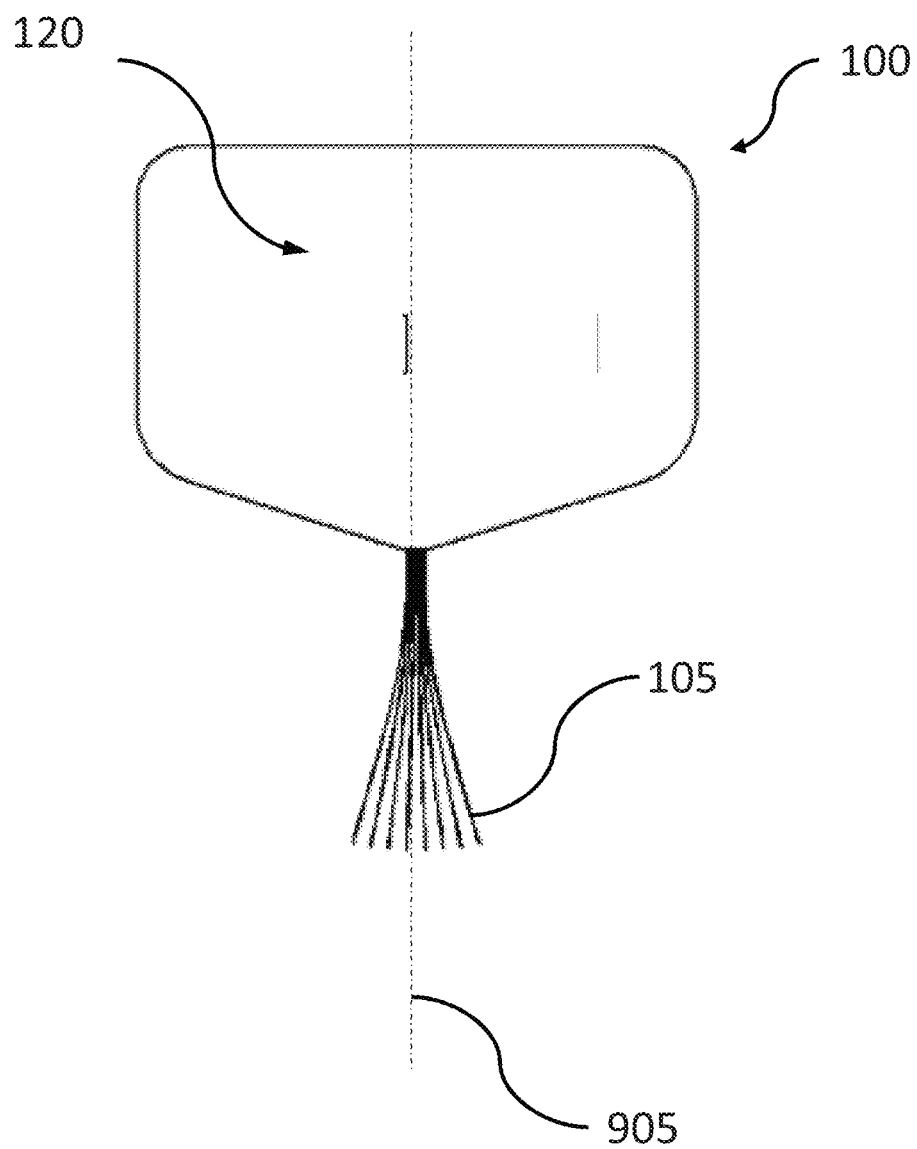
FIG. 8 shows an example embodiment (100) of the present invention having a plurality of neural interface probes (105) in contact with a connection body (120) wherein the neural interface probes have a geometric configuration in which the longitudinal axis of the probes is advantageously curved in a direction away from the center line (905) of the implantable microelectrode body (100.

In an embodiment of the invention related to methods of implantation, the neural interface probes have a geometric configuration in which the longitudinal axis of the probes is advantageously curved in a direction away from the center line (905) of the implantable microelectrode body (100) as shown in FIG. 8 in plan view. In FIG. 8, the present embodiment is shown having eight neural interface probes (105) with intrinsic curvature. As described for Prior Art carbon fiber electrodes (Gardner et al., U.S. application Ser. No. 14/902,734), when an implantable microelectrode body with a plurality of neural interface probes is withdrawn from water, the neural interface probes form a bundle in which the neural interface probes are weakly held together by van der Waals bonding. The bundle has a higher stiffness than an individual neural probe allowing penetration of the probe bundle into tissue during implantation without buckling of the bundle. As described in Gardner et al (U.S. application Ser. No. 14/902,734), the individual neural probes within a bundle will splay into tissue during implantation causing the interface pads to be distributed advantageously in a three-dimensional volume of tissue. In the present embodiment, a similar bundling and splaying behavior has been observed with amorphous silicon carbide neural interface probes. In contrast to Gardner et al., we have discovered that amorphous silicon carbide probes with intrinsic curvature will also form a bundle weakly held together by van der Waals bonding. The intrinsic curvature of the amorphous silicon carbide is advantageous in promoting splaying of the neural probes as they traverse tissue during implantation. A shortcoming of Prior Art implantable devices based on carbon fiber electrodes is the inability to fabricate neural probes from carbon fiber having intrinsic curvature.

In an embodiment of the present invention desirable for enhancing the spatial selectivity of neural recording and stimulation, a neural interface probe is configured to have a plurality of interface pads. A plan view of a neural interface probe (105) of the present embodiment having four interface pads (115) is shown in FIG. 9. Each interface pad (115) may be in contact with a metal trace also in contact with the amorphous silicon carbide insulation. Each interface pad may be connected to the ambient through an opening in the amorphous silicon carbide insulation. In some embodiments, thin film metal traces of the neural interface probe can extend to a communication circuit of the connection body (120), and, the communication circuit can include an electrical contact pad directly connected to the thin film metal trace. A perpendicular cross-sectional view of a neural interface probe of the present embodiment having four interface pads is shown in FIG. 10. In preferred embodiments, the number of interface pads on a neural interface probe may be in the range two to 16.

In an embodiment shown in FIG. 11 and advantageous in neural stimulation, two or more interface pads on a neural interface probe can be in contact with a common thin film metal trace. The thin film metal trace can extend to a communication circuit on the connection body. In a related embodiment shown in FIG. 12, an implantable neural interface device with a plurality of neural interface probes is configured to have a plurality interface pads on a plurality of the neural interface probes wherein the thin metal traces in contact with interface pads are electrically connected at a communication circuit of the connection body.

In an embodiment advantageous for neural stimulation and recording, shown in FIG. 13, the interface pad (115) is configured to be in contact with an electrode material (145) having desirable properties for stimulating and recording neural activity. The electrode material is further in contact with the ambient. Without limitation, such electrode materials include titanium nitride, iridium oxide, platinum, iridium, platinum-iridium alloy, palladium, and poly(ethylenedioxythiophene). In a related embodiment shown in FIG. 14, the electrode material (145) extends from the interface pad onto a portion of the surface of the amorphous silicon carbide (135) exposed to the ambient. A metal layer suitable for promoting adhesion may be disposed between the electrode material and the interface pad or between the electrode material and the amorphous silicon carbide insulation. Preferred metals for the adhesion promoting layer include, titanium, chromium, tungsten, and titanium-tungsten alloys.

In an embodiment of the invention, the connection body is configured to have an elongated structure in which the thin film metal trace or traces extend in the direction of the long axis of the connection body to a distant communication circuit. The elongated structure is advantageously configured to have flexibility in at least one direction perpendicular to the long axis of the connection body. A representative plan view of the present embodiment is shown in FIG. 15. This embodiment is advantageous in causing the connection circuit to be placed at a distance from the implantation site of the neural interface probes. Such advantages may include, without limitation, the ability to use large telemetry devices on the connection body without interfering with the function of the neural tissue or the ability to place the communication circuitry outside the body without the use of a telemetry device or without the need for implanted electrical connections between a wire or ribbon cable and the communication circuitry.

In an embodiment of the invention shown in FIG. 21, useful for interfacing to a three-dimensional volume of tissue, a plurality of neural interface devices (100) are configured in a parallel orientation with the connection bodies (120) of the neural interface devices in a face-to-face orientation. The connection bodies of the interface devices are separated by a solid spacer (195). The contacting surfaces of the spacer (195) and the connection bodies (120) are adhesively bonded with an epoxy, acrylic, or other bonding agent suitable for chronic implantation. In related embodiments the neural interface devices (100) may individually employ one or a plurality of neural interface probes (105); the neural interface probes may individually employ one or a plurality of interface pads (115), such interface pads being defined by openings in an amorphous silicon carbide layer of the neural interface probe and being connected to connection pads (125) by metal traces (not shown). There is no restriction on the number of neural interface devices that may be assembled in the manner shown in FIG. 21. Preferred embodiments employ from two to ten neural interface devices. The neural interface probes (105) of the present embodiment may be of different lengths and may be positionally offset between neural interface devices. Such positional offset allowing the neural interface probes to deflect out of the plane of the neural interface device without interfering with the neural interface probes on adjacent interface devices. All previously described embodiments of the neural interface devices are contemplated for use in the embodiment described in FIG. 21. The thickness of the spacer (195) separating individual neural interface devices may vary from about 0.005 mm to 1 mm. The spacers may be fabricated from many different materials suitable for implantable applications including polymers, metals, and ceramics. Preferred materials for the spacers include epoxy photoresists such as SU-8, which is well-known in the fabrication of implantable devices, alumina and polyimide.

As illustrated in FIG. 21, embodiments of neural interface device can further comprising a plurality of the implantable microelectrode bodies 100a, 100b, at least two of the implantable microelectrode bodies each having at least one of the neural interface probes 105. Each of the implantable microelectrode bodies 100a, 100b can further include a connection body (e.g., 120a, 120b respectively) surrounded by the amorphous silicon carbide insulation (e.g., a-SiC 135, FIG. 1). Each of the implantable microelectrode bodies 100a, 100b can be stacked in a face-to-face orientation such that a major plane of each of the connection bodies 120a, 120b (e.g., major planes 122a, 122b, respectively) are parallel to each other and the connection bodies 120a, 120b are separated from each other by one or more solid spacer layers 195.

Example 1

The following example describes the fabrication of an example implantable microelectrode body of the type shown in FIG. 15. In the example embodiment, the device has 8 neural interface probes (105) connected to a communication circuit on a connection body (120). The connection body is separated from the neural interface probes by a distance of approximately 50 mm. Referring to FIG. 16, in a first step, a single crystal wafer of silicon (150) with a diameter of 100 mm, is coated with a thin film of polyimide (155) having a thickness of about 1 micron. The polyimide layer is applied to the wafer by spin coating a polyimide precursor solution onto the wafer and curing the precursor at 350° C. for one hour in a nitrogen atmosphere to form the polymerized polyimide coating. In a second step, a first layer of amorphous silicon carbide (160) having a thickness of about 2 microns is then deposited over the polyimide layer by plasma enhanced chemical vapor deposition (PECVD) at a substrate temperature of 325° C., RF power density of 0.20 Wcm$^2$ (13.56 MHz), and pressure of 1000 millitorr using a reactive gas mixture of silane ($SiH_4$) and methane ($CH_4$) at flow rates of 12 sccm and 36 sccm respectively. The total gas flow rate into the PECVD reaction chamber is maintained at 800 sccm using argon as a carrier gas. In a third step, thin film metal traces (165) are formed on the first amorphous silicon layer by sputter deposition using lift-off photolithography to define the metal pattern. To facilitate liftoff, a non-photosensitive resist layer, known as lift off resist and a photosensitive resist layer are spin-coated consecutively on the first amorphous silicon carbide layer in a process designed to create an undercut in the two-layer resist. The two-layer resist is then exposed to ultraviolet radiation through a first photomask that defines the pattern of the metal traces on the neural interface probe and on the connection body of the device. The metal layer is deposited by DC sputtering and comprises a three-layer coating of titanium, gold, and titanium with respective thicknesses of 30 nm, 250 nm, and 30 nm. After metal deposition, the coated silicon wafer is immersed in a solution suitable for removing the resist layers and unwanted metal layers to create the desired thin film metal pattern. In a fourth step, a second layer of amorphous silicon carbide (170) having a thickness of about two microns is deposited over the metal traces and the first amorphous silicon carbide layer to provide complete insulation of the metal traces within amorphous silicon carbide. In a fifth step, openings (175) are formed in the second amorphous silicon carbide layer to expose the interface pads to the ambient and, on the connect body (120) of FIG. 15, to form openings for electrical contact pads (125) of FIG. 15. The interface pads are an integral part of the thin film metal layer (110) and the shape and size of the interface pad is determined by the shape and size of the opening in the second amorphous silicon carbide layer. The openings in the second amorphous silicon carbide layer are created by reactive ion etching (RIE) in a sulfur hexafluoride ($SF_6$) plasma at a pressure of four millitorr using an inductively coupled plasma (ICP) etcher. In the present devices, the openings for the interface pads are 2 microns by 50 microns resulting in an interface pad area of 100 micron$^2$. The etching of the second amorphous silicon carbide layer was limited to the interface pads and the electrical contact pads using a layer of photoresist patterned by exposure to ultraviolet light through a second photomask. In a sixth step, the external shape of the implantable microelectrode body is defined by removing all of the first and second amorphous silicon carbide layers that are not a desired part of the implantable body using a second reactive ion etching step in a pattern defined by a third photomask. In a seventh step, the coated silicon wafers are immersed in deionized water at 87° C. until the implantable microelectrode body (180) releases from the silicon wafer. Optionally, the released implantable microelectrode bodies are exposed to an oxygen plasma to remove the layer of polyimide in contact with the first silicon carbide layer. An optical image of an implantable microelectrode of Example 1 is shown in FIG. 17. The microelectrode comprises eight neural interface probes (105) connected to a connection body (120). The distal tip of each neural interface probe terminates in a symmetric triangular tip with an included angle of 10 to 14 degrees. Each neural interface probe has a thin metal trace (110) that extends from an interface pad near the distal tip of the neural probe to an electrical contact pad on the connection body. The geometric arrangement of electrical contact pads on the connection body is configured to align with contact pads on an electrical connector. Referring to FIG. 18, which is a magnified optical image of the distal tip of the implantable microelectrode body shown in FIG. 17, the neural interface probes (105) are formed into a bundle held together by van der Waals bonding. In a stated embodiment of the invention, the bundle is advantageous in minimizing buckling of the neural interface probes during implantation into tissue.

Example 2

Following the process outlined in Example 1, an implantable microelectrode body (100) having 16 neural interface probes (105), each of length 4 mm and suitable for implantation in brain, was fabricated. An optical image of the implantable microelectrode body is shown in FIG. 19. Each neural interface probe (105) is configured to have an interface pad (not shown) in contact with a thin film metal trace (110) extending to a connection body (120). At the connection body, the metal trace is connected to an electrical contact pad (125). In the present Example, electrical contact pads are configured to match with an electrical connector (185) suitable for interfacing with electronic equipment suitable for neural recording and stimulation. The electrical connector is mounted on the connection body (120) by solder joints (190) between the metal conductors on the connector to the electrical contact pads exposed by openings in the second silicon carbide layer.

Example 3

Referring to FIG. 1, the present example demonstrates a feature of the implantable neural interface device (100) that is advantageous for insertion of neural interface probes (105) of the neural interface device into tissue. Using the PECVD and RIE methods described in Example 1, an amorphous silicon carbide neural interface probe (105) with transverse cross-sectional dimensions of 6 microns by 8 microns and a probe length of 2 mm was fabricated. The neural interface probe (105) thus has a transverse cross-sectional area of 48 microns. The connection body of the neural interface probe is attached to an apparatus that provides insertion of the neural interface probe into brain at a controlled speed. The apparatus further measures the force required to insert the neural interface probe into tissue. The probe was inserted into the exposed brain of a rat to a depth of approximately 1.5 mm without buckling. The force to penetrate the surface of the rat brain was determined to be 0.35 mN and the maximum force recorded during insertion was 1.5 mN.

Those skilled in the art to which this application relates will appreciate that other and further additions, deletions, substitutions and modifications may be made to the described embodiments.

What is claimed is:

1. A method of manufacturing neural interface device, comprising:
　　forming one or more neural interface probes of an implantable microelectrode body, including:
　　　　plasma enhanced chemical vapor deposition of a first amorphous silicon carbide insulation layer on a release layer;
　　　　forming a photoresist layer on the first amorphous silicon carbide insulation layer, forming an opening in the photoresist layer to expose a portion of the first amorphous silicon carbide insulation layer, depositing a metal layer on the photoresist layer and through the opening onto the portion of the first amorphous silicon carbide insulation layer and then removing the photoresist layer and the metal layer thereon, leaving the thin film metal trace on the portion of the first amorphous silicon carbide insulation layer;

plasma enhanced chemical vapor deposition of a second amorphous silicon carbide insulation layer on the first amorphous silicon carbide insulation layer and covering the thin film metal trace on the portion of the first amorphous silicon carbide insulation layer;

forming an opening in the second amorphous silicon carbide insulation layer to expose a portion of the thin film metal trace to an ambient environment surrounding the neural interface device and thereby define an interface pad;

patterning the first amorphous silicon carbide insulation layer and the second amorphous silicon carbide insulation layer to define the one or more neural interface probes, wherein:

a cross-sectional area perpendicularly transverse to a long axis length of the one or more neural interface probes and through any perpendicularly transverse cross-section along the long axis length is less than 100 microns$^2$, and the first amorphous silicon carbide insulation layer and the second amorphous silicon carbide insulation layer are a principle material of construction of the one or more neural interface probes such that at least 85 percent of a total area any one of the cross-sections along the long axis length is composed of the first amorphous silicon carbide insulation layer and the second amorphous silicon carbide insulation layer.

2. The method of claim 1, wherein:

the plasma enhanced chemical vapor deposition conditions of the first and second amorphous silicon carbide insulation layers further comprising:

providing a temperature in a range from 200 to 400° C., providing a deposition pressure in a range from 800 to 1200 millitorr, providing a reactive gas mixture comprised of silane (SiH$_4$) and methane (CH$_4$), with a molar compositional ratio (SiH$_4$:CH$_4$) in a range from 1:2 to 2:1, providing a carrier gas, and setting a total flow rate of the reactive gas mixture plus the carrier gas in a range from 600 to 1200 sccm; and the forming of the thin film metal trace and the interface pad includes a physical vapor deposition process including:

sputtering with an inert gas plasma at a pressure in a range from 1 and 40 millitorr, or, thermal evaporation at an ambient deposition temperature.

3. The method of claim 1, wherein each of the first and the second amorphous silicon carbide insulation layers have a thickness in a range from 0.1 and 4 microns, and each of the first and the second amorphous silicon carbide insulation layers have a compressive residual stress in a range from 50 to 200 MPa.

4. The method of claim 1, wherein:

the thin metal trace has a thickness in a range from 0.1 and 2 microns, and the thin metal traces have a residual stress in a range from 100 MPa in compression to 500 MPa in tension.

5. The method of claim 1, further including releasing the recite layer from the first amorphous silicon carbide insulation layer by immersion in water.

* * * * *